United States Patent [19]

Hudson

[11] Patent Number: 4,935,536
[45] Date of Patent: Jun. 19, 1990

[54] PROTECTING GROUPS FOR ASPARAGINE AND GLUTAMINE IN PEPTIDE SYNTHESIS

[75] Inventor: Derek Hudson, San Anselmo, Calif.

[73] Assignee: Millipore Corporation, Bedford, Mass.

[21] Appl. No.: 316,570

[22] Filed: Feb. 27, 1989

Related U.S. Application Data

[63] Continuation of Ser. No. 52,321, May 21, 1987, abandoned.

[51] Int. Cl.$^5$ .............................................. C07C 125/06
[52] U.S. Cl. ......................................... 560/29; 560/39; 562/448
[58] Field of Search ...................... 562/448; 560/39, 29

[56] References Cited

U.S. PATENT DOCUMENTS 2,873,294   2/1959   Kline ..................................... 562/448
3,903,147   2/1975   Kyncl et al. ......................... 562/448
4,716,232  12/1987   Teransky .............................. 548/110

OTHER PUBLICATIONS

Weygand et al., Chem. Ber., vol. 101: 3642-3648 (1968).
Weygand et al., Chem. Ber., 101, pp. 3623-3641 (1968).

Primary Examiner—James H. Reamer
Attorney, Agent, or Firm—Hamilton, Brook, Smith & Reynolds

[57] ABSTRACT

Trialkoxybenzyl (Taob) protected asparagine and glutamine, a method of synthesis and a method of use are provided. The Taob protected Asn and Gln have the following formulae:

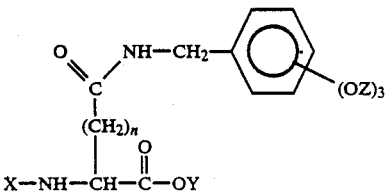

or

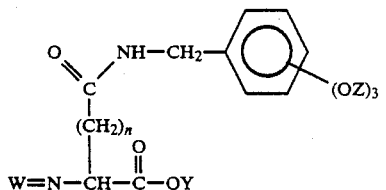

wherein Z is an alkyl group having from 1 to 10 carbon atoms; X and W are any α-protecting group which can be selectively removed while maintaining Taob intact; Y is H or any group sufficiently active or activatable to react with $NH_2-$ or $NH=$ to generate an amide bond; n is 1 for asparagine or 2 for glutamine. These derivatives are stable in solution, have good solubility in organic solvents and couple directly without side reactions.

6 Claims, 7 Drawing Sheets

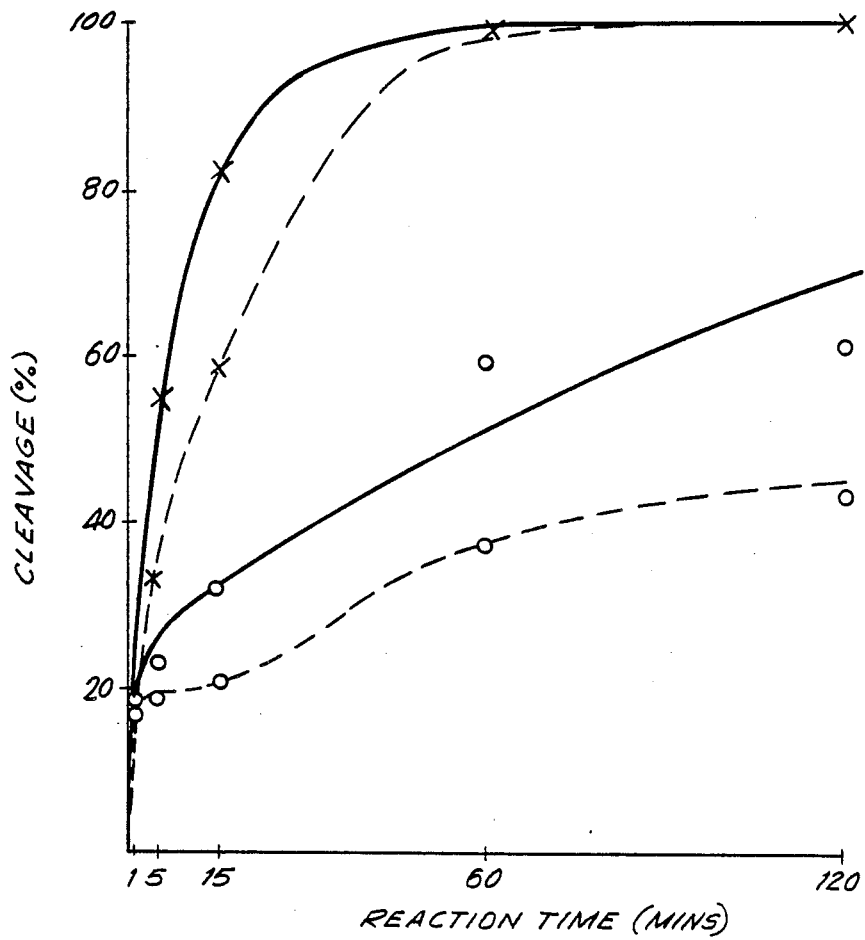

PROTECTING GROUPS FOR ASPARAGINE AND GLUTAMINE IN PEPTIDE SYNTHESIS

This is a continuation of co-pending application Ser. No. 07/052,321 filed on May 21, 1987, now abandoned.

BACKGROUND OF THE INVENTION

This invention relates to new protecting groups for asparagine and glutamine in solid phase peptide synthesis and more particularly to trialkoxy benzyl protecting groups for protection of the asparagine and glutamine residues. Solid phase peptide synthesis typically begins with covalent attachment of the carboxyl end of a first alpha-amine protected acid through an organic linker to an insoluble resin synthesis bead. This can be illustrated as:

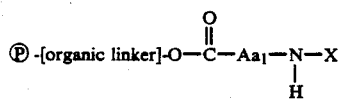

wherein P is the insoluble synthesis resin, $Aa_1$ is the first amino acid and X is a protecting group such as Fmoc, t-Boc and the like.

The general synthesis cycle then consists of deprotection of the alpha-amine group of the last amino acid, washing and, if necessary, neutralization, followed by reaction with a carboxyl activated form of the next alpha-amine protected amino acid to be added. The peptide chain then becomes:

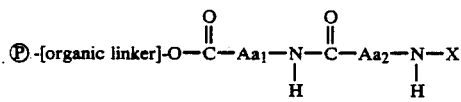

wherein $Aa_2$ is the second amino acid. The cycle is repeated to the nth amino acid to yield:

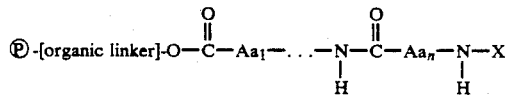

wherein $Aa_n$ is the $n^{th}$ amino acid.

Each successive amino acid is attached to the terminal nitrogen by the carbonyl carbon of the carboxylic acid group. Addition of asparagine and glutamine acid residues present particular problems because each have an amide side chain in addition to the amino acid group. The structural formulae are as follows:

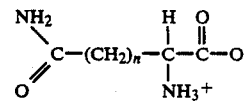

wherein asparagine is shown when n is 1 and glutamine when n is 2.

FIG. 1 is a diagrammatic representation of a peptide synthesis apparatus suitable for automated computer controlled solid phase synthesis. Such apparatus are available from Biosearch, Inc. of San Rafael, Calif.

Present automatic peptide synthesizers conventionally involves preactivation of a protected amino acid utilizing Diisopropylcarbodiimide (DIPCDI). The synthesis is carried out in a reaction vessel 11 which includes a synthesis resin 12 therein. Reaction vessel 11 is coupled to a source of protected amino acid 13 and a source of DIPCDI activator 14, in a solvent such as $CH_2Cl_2$. Protected amino acid from amino acid reservoir 13 is fed to reaction vessel 11 through a line 18 by an amino acid control valve 16 and DIPCDI activator is fed into line 18 and mixed with the amino acid by an activator valve 17. Amino acid valve 16 and activator valve 17 are activated in brief alternate intervals so that protected amino acid and DIPCDI activator are mixed in line 18 for a preselected time prior to being fed into reaction vessel 11.

After the coupling reaction under a nitrogen atmosphere in reaction vessel 12 is complete, the protected amino acid now coupled through its carboxylic acid group to synthesis resin 12 is deblocked with, for example trifluoroamine (TFA), washed with a base and the next activated amino acid residue is added to reaction vessel 11. Upon obtaining the desired peptide residue, the peptide is cleaved from synthesis support 12, generally with hydrofluoric acid (HF).

In conventional t-Boc solid phase peptide synthesis, addition of asparagine and glutamine is performed using diisopropylcarbodiimide (DIPCDI) or dicyclohexylcarbodiimide (DCCI) coupling in the presence of 1-hydroxybenzotriazole (HOBt). The protocol is:

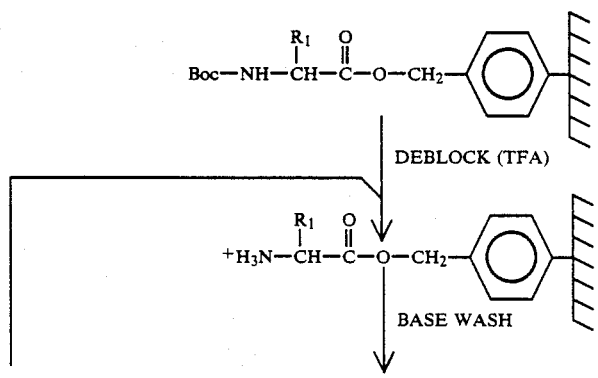

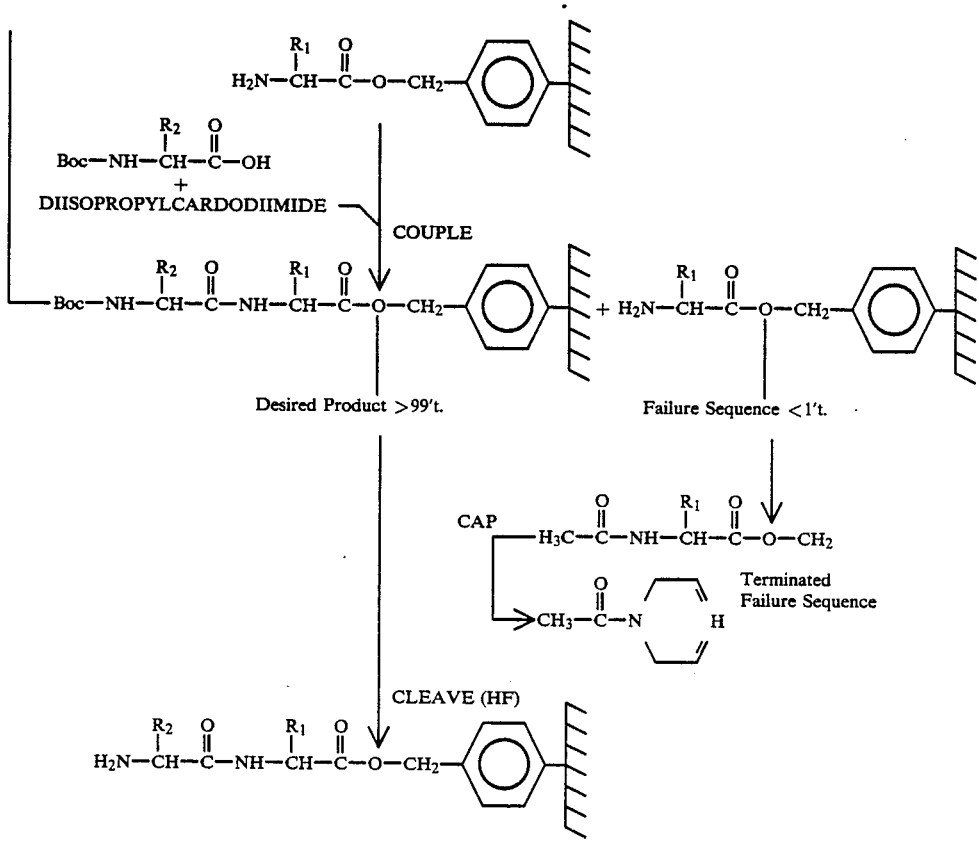

When the derivatives and additives are dissolved in dimethylformamide (DMF) at 0.4M concentration and mixed in-line with DIPCDI, no precipitation occurs and couplings proceed well without significant dehydration of the amide side chains to the corresponding nitriles. Xanthenyl derivatives, on the other hand, are less soluble and the active intermediates crystallize rapidly during in-line mixing causing poor coupling and clogging of valves in automated synthesizers.

Alternatively, Fmoc mediated solid phase peptide synthesis can be performed using the following protocol:

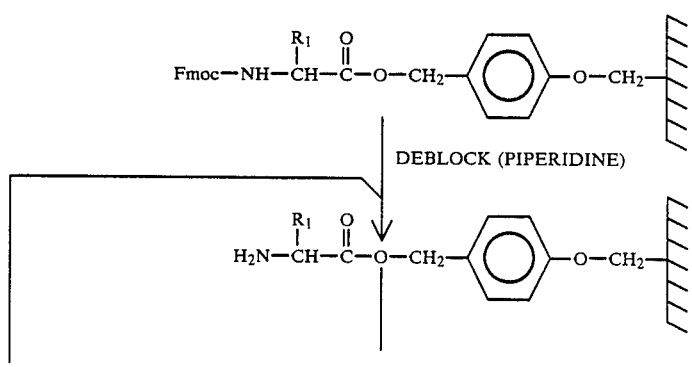

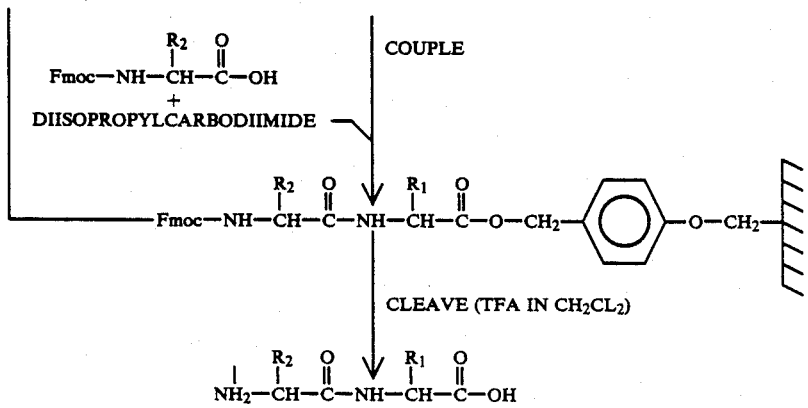

Unprotected derivatives of asparagine and glutamine are very insoluble in Fmoc mediated solid phase peptide synthesis. Only a 0.2M solution of Fmoc-Asn-OH in DMF can be prepared and precipitation occurs when the Fmoc protected asparagine is mixed with DIPCDI and HOBt. In the case of Fmoc protected glutamine, complete solution is not effected even after prolonged sonication at 0.2M.

The use of pentafluorophenyl esters to increase solubility has been proposed and is effective in the case of Fmoc protected asparagine resulting in good coupling. However, Fmoc-Gln-OPFP is still completely insoluble and poor coupling is observed. Furthermore, sampling of stored DMF solutions of active esters is not possible because racemisation, dehydration and dimer formation occur albeit at slow rates. This slow dissolution and poor solubility of the active esters complicates operation and limits performance.

Sequences containing Asn-X and Gln-X wherein X is a non-hindered amino acid residue tend to form cyclic imides under acidic or basic conditions. These cyclic imides can open to lead to deamidated alpha and beta peptides. In slow couplings containing N-terminal unprotected Gln, pyroglutamyl formation gives rise to a significant amount of chain termination. Sequences rich in Asn and Gln are formed at slow rates due to the tendency for interpeptide hydrogen bonding to occur causing interpeptide aggregation and reduced coupling efficiency. Such interpeptide hydrogen bonding sterically masks the amino groups.

Other problems include the occurrence of dehydration side reactions on activation that result in nitrile containing byproducts. Finally, the poor solubility of these derivatives even in DMF is the most serious problem and is just as apparent with pentafluorophenyl and other active ester derivatives as with the free acids themselves.

These problems are also directly applicable to Dts mediated syntheses even though some of the side reactions are minimized under neutral conditions. Dts-Asn-OH and Dts-Gln-OH are only slightly soluble in inorganic solvents resulting in yields from polyethylene glycol xanthate mediated syntheses of only about 20%.

Attempts have been made to protect the amide side chain using dimethoxybenzhydryl protecting groups (Mbh). However, Mbh protection provides only poor yields and requires relatively drastic cleavage conditions.

Accordingly, it is desirable to provide an improved protecting group for use on the amide side chain in Asn and Gln in solid phase peptide synthesis.

SUMMARY OF THE INVENTION

Generally speaking, in accordance with the invention, new trialkoxybenzyl protecting groups for asparagine and glutamine in solid phase peptide synthesis are provided. The protecting group is a trialkoxybenzyl radical having the general formula

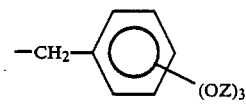

wherein Z is an alkyl group having from one to about 10 and preferably from one to about three carbon atoms, such as methyl, ethyl, n-propyl, iso-propyl and the like. Preferably, the alkoxy group is methoxy and the protecting group is called Tmob. The trialkoxybenzyl protected Asn and Gln have the following formulae:

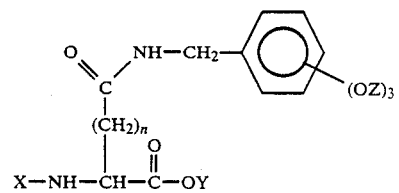

or

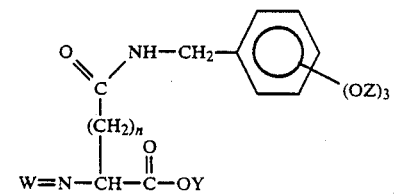

wherein X is Fmoc, Bpoc, Poc, benzyloxycarbonyl (Z) or any protecting group which can be selectively removed while maintaining the trialkoxybenzyl derivative intact; W is dithiosuccinoyl (Dts=), phthaloyl or other bidentate protecting group which can be selectively removed while maintaining the trialkoxybenzyl derivative intact; Y is H, benzotriazolyl, pentafluorophenyl, nitrophenyl, trichlorophenyl or any group sufficiently active or activatable to react with NH₂— or NH= to generate an amide bond; n is 1 for asparagine or 2 for glutamine; and Z is selected from alkyl groups having from 1 to 10 carbon atoms and wherein Z is either a single choice or a combination.

Fmoc-Asn(Tmob)-OH and Fmoc-Gln(Tmob)-OH can be synthesized in high yield and purity. These protected Asn-Gln derivatives are stable in DMF solution, exhibit good solubility in organic solvents and couple directly without side reactions. The trialkoxybenzyl group is cleaved with a half life of less than one minute in 95% trifluoroacetic acid (TFA). Acyl carrier proteins such as the 65-74 sequence and other peptides have been synthesized rapidly and in high yield using these derivatives. Addition of dimethylsulfide effectively suppresses alkylation side reactions during removal of protecting groups.

Accordingly, it is an object of the invention to provide improved protecting groups for asparagine and glutamine.

It is another object of the invention to provide trialkoxybenzyl protecting groups for asparagine and glutamine in solid phase peptide synthesis.

A further object of the invention is to provide trialkoxybenzyl protected asparagine and glutamine.

Still another object of the invention is to provide a method of synthesis of Fmoc-Asn(Tmob)-OH and Fmoc-Gln(Tmob)-OH.

Still other objects and advantages of the invention will in part be obvious and will in part be apparent from the specification.

The invention accordingly comprises the novel compounds disclosed, the several steps and the relation of one or more of such steps with respect to each of the others, and the compositions possessing the features, properties, and the relation of constituents, which are exemplified in the following detailed disclosure, and the scope of the invention will be indicated in the claims.

DESCRIPTION OF THE DRAWINGS

For a fuller understanding of the invention, reference is had to the following description taken in connection with the accompanying drawings, in which:

FIG. 4 is a graph showing the rate of acidolytic cleavage of protecting groups from Asn(Tmob) and Gln(Mbh).

DESCRIPTION OF THE PREFERRED EMBODIMENTS

Figure 1:
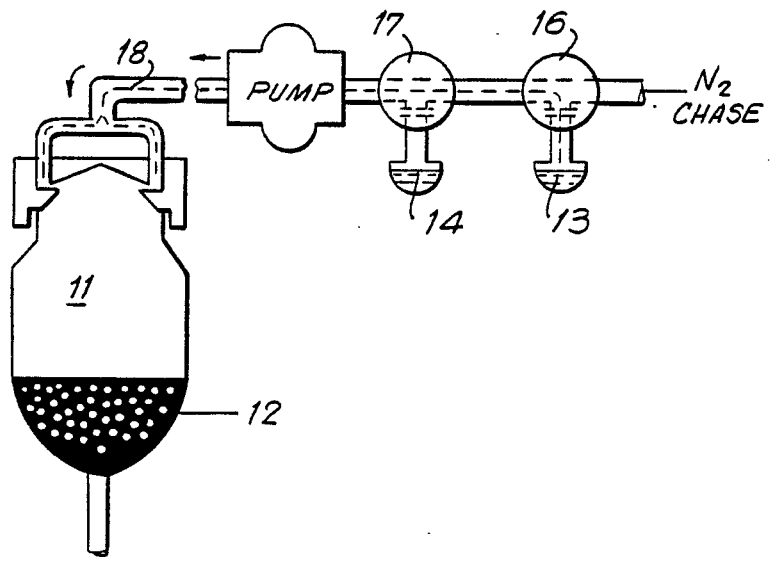
FIG. 1 is a diagrammatic illustration showing an apparatus for performing automated solid phase peptide synthesis suitable for use in accordance with the invention.
Figure 2A:
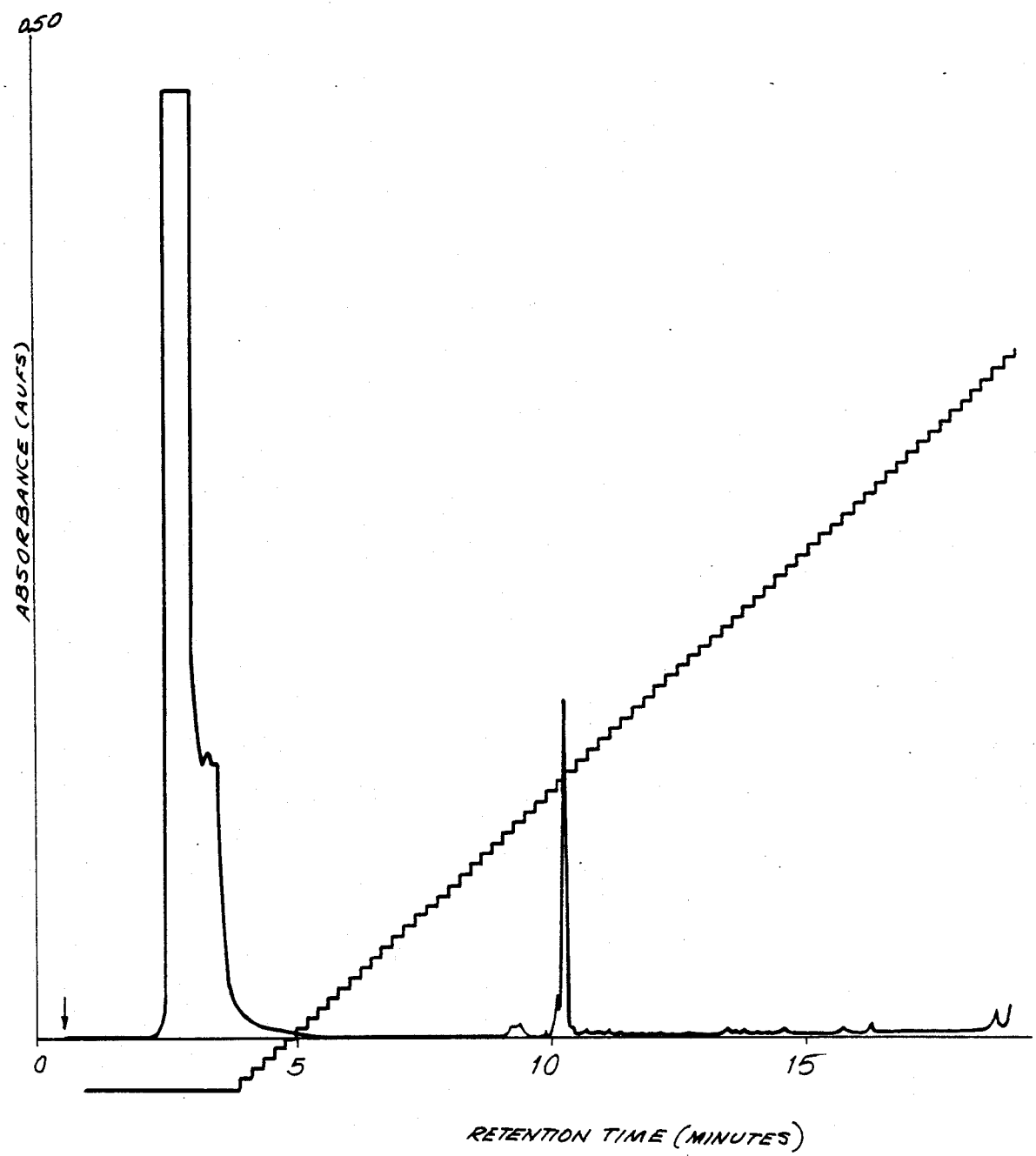
FIGS. 2A, 2B, 2C and 2D are HPLC profiles of acyl carrier protein 65-74 sequence synthesized on various supports.
Figure 2B:
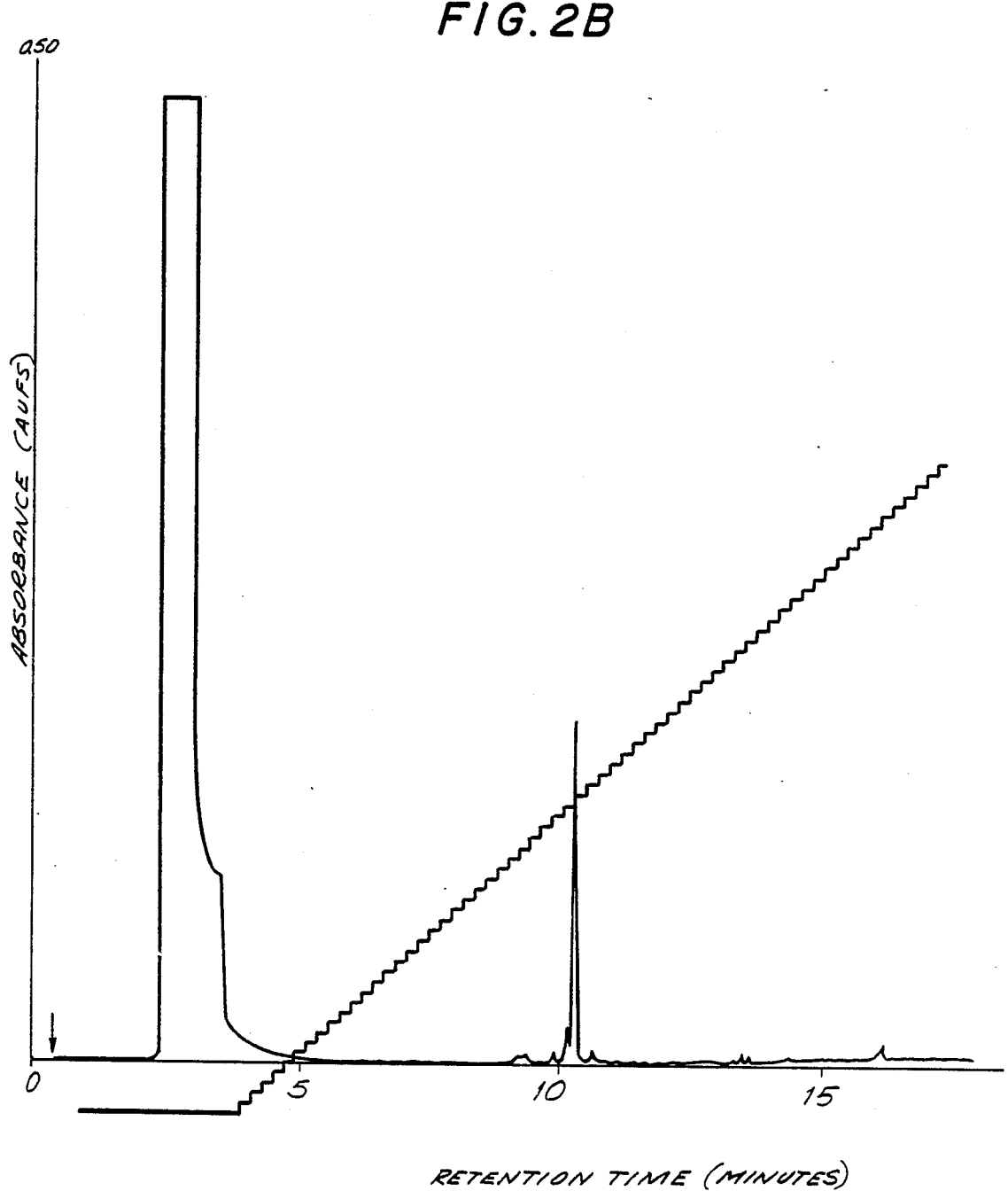
Figure 2C:
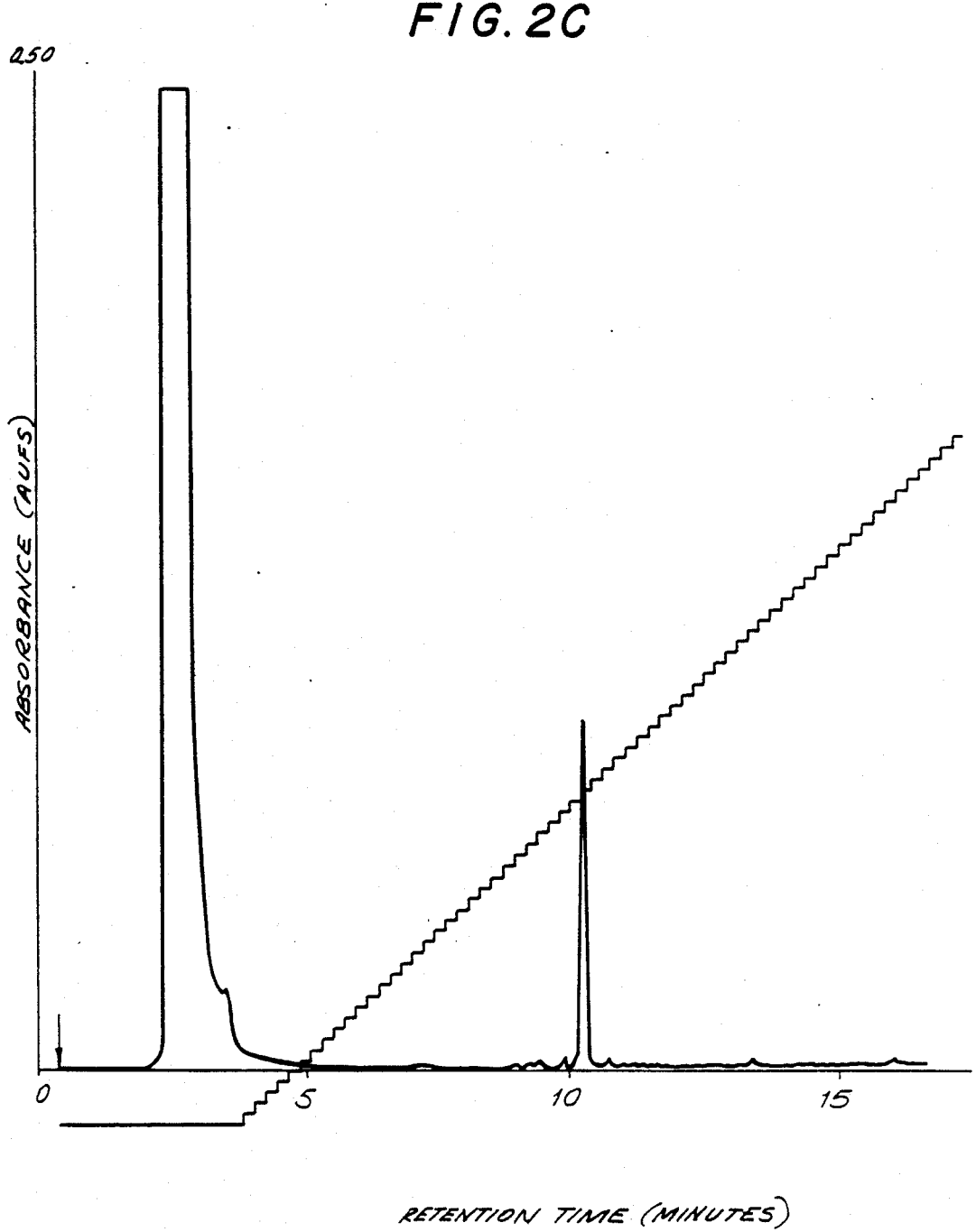
Figure 2D:
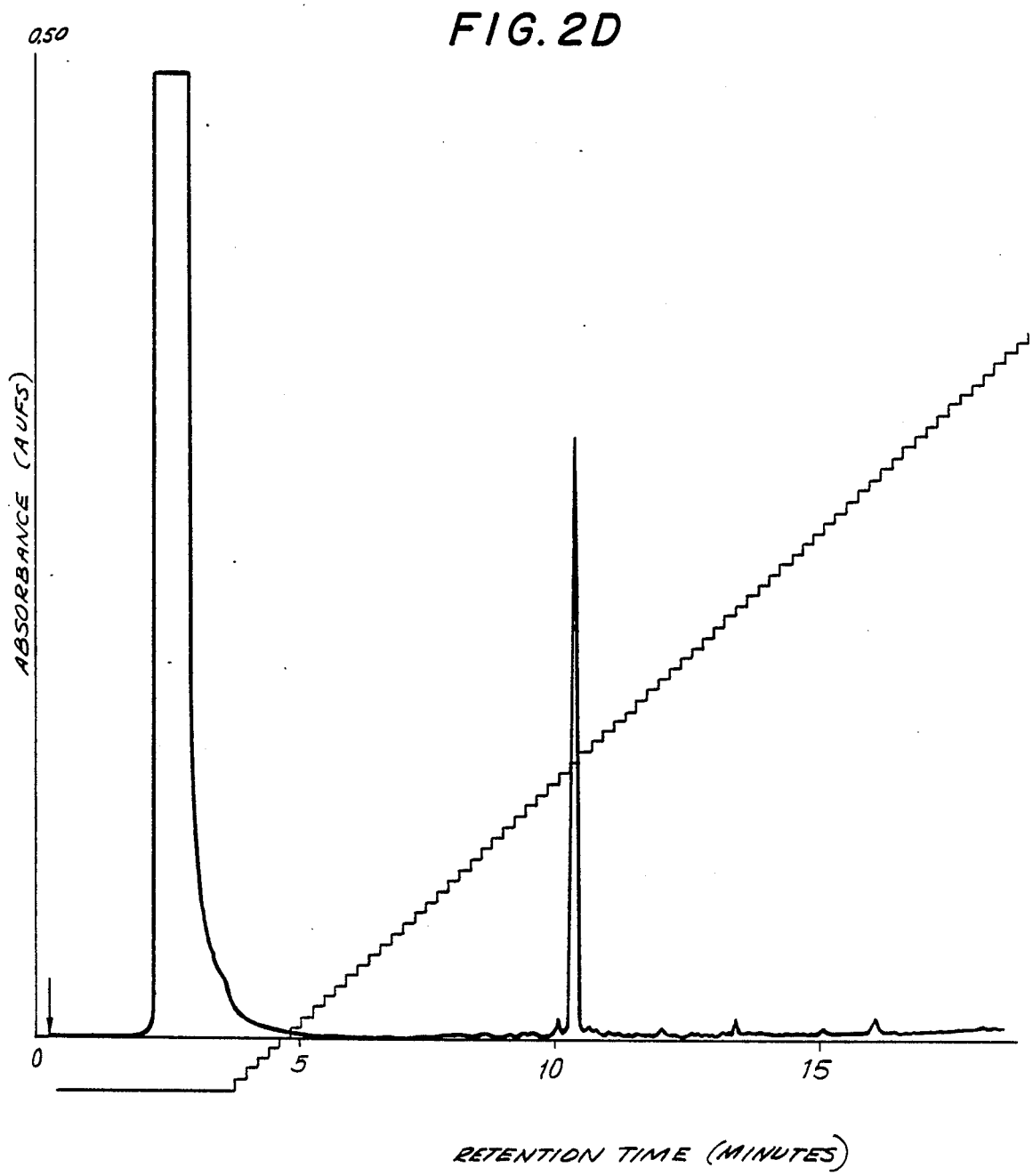

Fmoc-Asn(Tmob)-OH and Fmoc-Gln(Tmob)-OH were synthesized in high yield and purity from commercially available starting materials as follows:

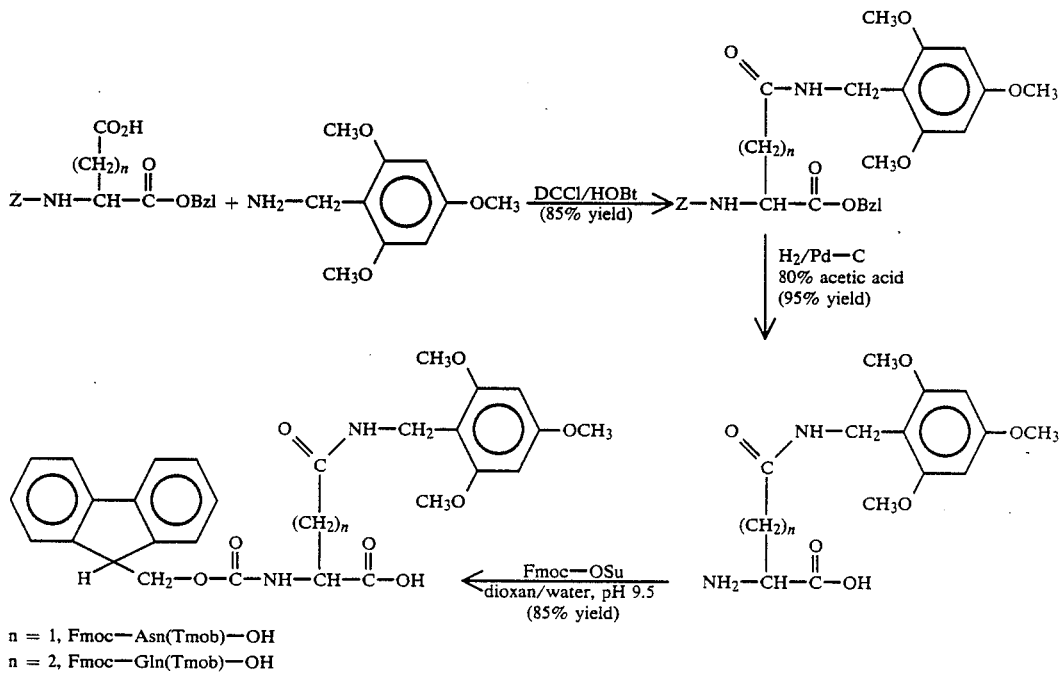

n = 1, Fmoc—Asn(Tmob)—OH
n = 2, Fmoc—Gln(Tmob)—OH

The alpha benzyl esters of Z-L-aspartic and Z-L-glutamic acids were coupled with 2,4,6-trimethoxybenzylamine using the DCCI/HOBt method with free protected amino acids obtained by catalytic hydrogenation in 80% acetic acid. There is no evidence of lability of the Tmob groups under these conditions. Further derivation to give the desired product was performed using an Fmoc succinimide reagent.

Although 2,4,6-trimethoxybenzylamine is commercially available, the 2,4,6-trimethoxybenzylamine derivative can be synthesized from 2,4-dimethoxyphenol. In this case, the 2,4,6-trimethoxybenzylamine is synthesized as follows:

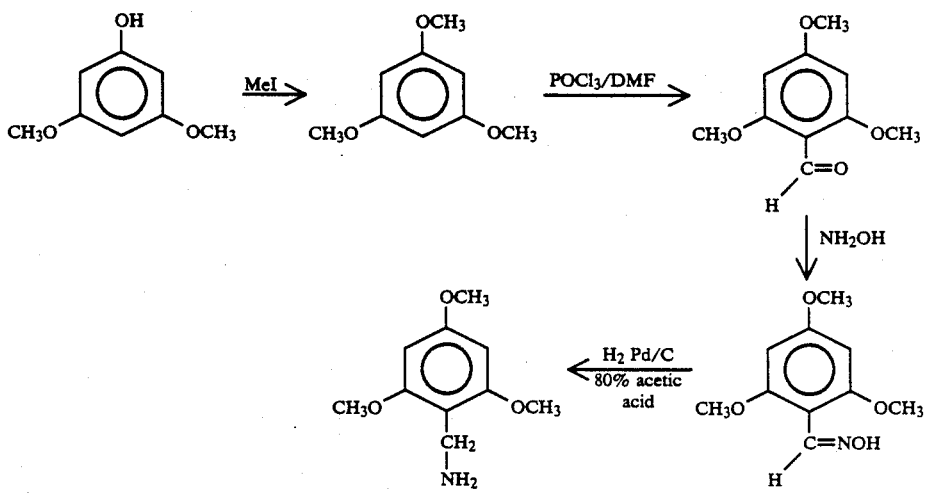

The 2,4,6-trimethoxybenzylamine derivative is then condensed with either N-benzyloxycarbonyl aspartic acid or N-benzyloxycarbonyl glutamic acid alpha benzyl esters (obtained from Chemical Dynamics) to give the protected intermediates which are nicely crystalline, form in good yield and have good solubility in organic solvents. The solubility of the protected intermediates is used to predict the solubility of the desired Fmoc derivatives.

When a sample of the Gln intermediate was treated with a 7:3 solution of TFA/DCM, an intense yellow-orange color developed rapidly and remained unchanged after 15 minutes. This intense yellow-orange color was due to the formation of the expected stable and chromomorphic trimethoxybenzylcarbonium ion. TLC showed rapid deprotection with no generation of benzyloxycarbonyl glutamic acid alpha benzyl ester.

The protected acid derivatives can be hydrogenated for 2 hours in 80% acetic acid to give the desired substituted Asn(Tmob) and Gln(Tmob) derivatives. There is no indication of the presence of Asn or Gsn. This is important because reduction or premature acidolysis would lead to these residues as impurities.

Treatment of the Gln(Tmob) derivative with 95% TFA was followed quantitatively by Amino Acid Analysis (AAA). The half life of cleavage was less than 1 minute, although some remained after 5 minutes and none was detected at 15 minutes. There was no Gln present. It can therefore be concluded that the Tmob group is stable in 80% acetic acid, but is removed rapidly with TFA. Even in Asn and Gln rich sequences, the normal 2 hour treatment with TFA used for cleavage should totally remove all Tmob groups.

The last step of the synthesis of the Tmob protected acid involved reaction with Fmoc-OSu in a 1:1 solution of dioxan:water at pH 9. The reactions were rapid and the crude products looked very good. Recrystallization from DCM/ethyl acetate/petrol entirely removed all impurities. The products were totally and rapidly soluble in DMF at 0.4M and no precipitation occurred when the products were mixed with DIPCDI in DSM.

The following Examples show preparation of Fmoc-Asn-Tmob-OH and Fmoc-Gln-Tmob-OH. These examples are presented for purposes of illustration only and are not intended to be construed in a limiting sense.

Example 1 - Preparation of Fmoc-Asn(Tmob)-OH

Step 1: N-Benzyloxycarbonyl-(N'-2,4,6-trimethoxybenzyl)-L-asparagine alpha benzyl ester N-Benzyloxycarbonyl-L-aspartic acid alpha benzyl ester (Chemical Dynamics, 17-6882-00, 1.785 g, 5 mmol) and 1-hydroxybenzotriazole (1.15 g, 7.5 mmol) were dissolved in 1:1 DMF-dichloromethane (20 ml), and the stirred solution cooled to 0 degrees. 2,4,6-trimethoxybenzylamine hydrochloride (Aldrich 30,098-5; 1.40 g, 5.5 mmol) was added, followed in turn by triethylamine (0.77 ml, 5.5 mmol) and dicyclohexylcarbodiimide (1.133 g, 5.5 mmol). The solution was maintained at 0 degrees for 2 hours and then slowly warmed to room temperature and stirred overnight. The resulting suspension was filtered and the precipitate washed with ethyl acetate. The combined filtrates were evaporated to dryness and the residue dissolved in dichloromethane (50 ml). This solution was washed with ice cold 5% citric acid solution (2x), resulting in some crystallization in the aqueous phases. The solution was further washed with water (1x), 1M sodium bicarbonate solution (3x) and water (3x). The dichloromethane was evaporated and the residue recrystallized from ethyl acetate/petrol to give 2.55 g, 88%, tlc:-single spot Rf 0.75 chloroform/methanol/acetic acid (95:2.5:2.5), m.p. 136 degrees.

Step 2: N'-(2,4,6-trimethoxybenzyl)-L-asparagine

The fully protected derivative Z-Asn(Tmob)-OBzl prepared in Step 1 (2.0 g, 3.75 mmol) was dissolved in acetic acid (50 ml), water (14 ml) and DMF (10 ml) by slight warming and vigorous stirring, nitrogen was flushed through the low pressure hydrogenation flask, 5% palladium on carbon catalyst (400 mg) was added, and a gentle stream of hydrogen continuously passed over the vigorously stirred solution for 2 hours. Nitrogen was once more flushed through the system and the catalyst removed by filtration through a doubled fluted Whatman No. 1 filter paper. The filtrate was evaporated, the residue dried in vacuo, and triturated under ethyl acetate to give a white solid. The suspension was cooled overnight to 4 degrees, then filtered and washed with ethyl acetate. Yield after drying 1.16 g (96%), Rf 0.55 single spot n-butanol/acetic acid/water (3:1:1).

Step 3: N-fluorenylmethyloxycarbonyl-N'(2,4,6-trimethoxybenzyl)-L-asparagine, Fmoc-Asn(Tmob)-OH N'-(Trimethoxybenzyl)-L-asparagine (0.93 g, 3 mmol) was stirred in 1:1 dioxan/water (10 ml) and concentrated KOH solution added to achieve pH 9 (not totally soluble). A solution of F-moc-succinimide (1.041 g, 3.09 mmol) in dioxan (5 ml) was added dropwise over 30 minutes, the pH being maintained at 9 by the addition of concentrated KOH solution. After 2 hours water (25 ml) was added, the mixture cooled in an ice bath, and solid citric acid added to pH 3 precipitating a white solid. Ethyl acetate (40 ml) and n-butanol (10 ml) were added and the mixture shaken. The lower phase was extracted once more (ethyl acetate 25 ml, n-butanol 5 ml), and the organic layers combined. These were washed with water (2x), saturated salt solution (1x), dried over magnesium sulfate and evaporated. The crystalline residue was dissolved in warm methylene chloride/ethyl acetate (1:1, 50 ml) and petrol was added (20 ml). The turbid solution was refrigerated overnight, and the crystals collected, washed with petrol and dried to give, in 2 crops from the recrystallization, 0.88 g (58%), thin layer chromatography 1 spot Rf 0.35 chloroform/methanol/acetic acid (90:5:5).

Example 2 - Preparation of Fmoc-Gln(Tmob)-OH

Step 1: N-benzyloxycarbonyl-(N'-2,4,6-trimethoxybenzyl)-L-glutamine alpha benzyl ester.

N-benzyloxycarbonyl-L-glutamic acid alpha benzyl ester (Chemical Dynamics, 17-7048-00, 1.855 g, 5 mmol) was coupled with 2,4,6-trimethoxybenzylamine as described in Step 1 of Example 1 and following an identical work up gave 2.15 g, 75% of the desired derivative, single spot Rf 0.70 chloroform/methanol/acetic acid (90:5:5), m.p. 137–138 degrees.

Step 2: (N'2,4,6-trimethoxybenzyl)-L-glutamine

The fully protected derivative, Z-Gln(Tmob)OBzl (2.0 g, 3.65 mmol) was hydrogenated and worked up as described in Step 2 of Example 1 to give 1.08 g (94%), Rf 0.55 single spot n-butanol/acetic acid/water (3:1:1).

Step 3: Rate and Selectivity of Cleavage of Tmob Protection

N'(2,4,6-trimethoxybenzyl)-L-glutamine (6.5 mg, 20 micromol) was dissolved in 95% trifluoroacetic acid. A yellow-orange color rapidly developed. Samples (10 microlitres) were removed after 1, 5, 15, 60 and 120 minutes. These were immediately diluted with water, frozen and lyophilized. Quantitative amino acid analysis showed the rapid liberation of glutamine, eluting at 11.45 minutes on an LKB Alpha Plus Amino Acid Analyser, with no formation of glutamic acid. A peak at 38.02 minutes due to the Gln(Tmob) rapidly decreased in proportion and could not be detected at 15 minutes. The half life of the reaction was less than 1 minute.

Step 4: N-fluorenylmethyloxycarbonyl-N'(2,4,6-trimethoxybenzyl)-L-glutamine, Fmoc-Gln(Tmob)-OH N'(2,4,6-trimethoxybenzyl)-L-glutamine (0.97 g, 3 mmol) was reacted with Fmoc-succinimide as described in Step 3 of Example 1 to give 1.23 g (78%), thin layer chromatography 1 spot Rf 0.35 chloroform/methanol/acetic acid (90:5:5).

Adequately concentrated solutions (>4M) of Fmoc-Asn(Tmob)-OH prepared in Example 1 and Fmoc-Gln(Tmob)-OH prepared in Example 2 in DMF are readily prepared. The solubility in methylene chloride was somewhat lower, but can be increased by addition of a small amount of DMF. No detectable decomposition is observed 3 days after preparation of the solutions.

Synthesis of aggregation prone acyl carrier proteins can be performed using the Asn(Tmob) and Gln(Tmob) derivatives on an encapsulated polydimethyl acrylimide support. Single 15 minute couplings are achieved by a direct diisopropylcarbodiimide method. Following cleavage with 95% TFA for 2 hours, the product is isolated in high yield. HPLC amino acid analysis and FAB mass spectrometry confirms the efficiency of the synthesis.

The following Example shows preparation of the aggregation prone acyl carrier protein 65–74 sequence (H-Val-Gln-Ala-Ala-Ile-Asp-Tyr-Ile-Asn-Gly-OH sequence. This Example is presented for purposes of illustration only and is not intended to be construed in a limiting sense.

Example 3 - Preparation of H-Val-Gln-Ala-Ala-Ile-Asp-Tyr-Ile-Asn-Gly-OH

The ACP decapeptide was prepared by the simultaneous macrocolumn reactor method. Supports were packed in glass macro-columns and filled and emptied using syringes. The columns were shaken periodically with wrist action to obtain efficient mixing. The method allows simultaneous synthesis with the same lots of reagents, the same times and the same temperatures. This allows meaningful comparisons to be made. For purposes of this experiment, six runs were performed using Waters Poracil Type B-an HPLC silica (Runs A and B), MBHA-a polystyrene (Runs C and D) and Pepsyn K (Runs E and F) as supports.

The six Fmoc-Gly derivatized supports were placed in separate Biosearch Model 8600 Macrocolumn reactors and simultaneously taken through the following synthesis procedure: DMF washes (2x), Fmoc removal using 30% piperidine in DMF (1 min, 10 min), DMF washes (6x), coupling at a final concentration of 0.2M (20 minutes for Asn; 15 minutes for all other couplings). Fmoc-Asn(Tmob)-OH was coupled in the first cycle; subsequent cycles added Fmoc-Ile-OH, Fmoc-Tyr(-Bu$^t$)-OH, Fmoc-Asp(OBu$^t$)-OH, Fmoc-Ile-OH, Fmoc-Ala-OH, Fmoc-Ala-OH, Fmoc-Gln(Tmob)-OH and Fmoc-Val-OH. At the end of the synthesis the final Fmoc group was removed using 30% piperidine (1 and 10 min), the supports washed with DMF (6x) and methylene chloride (6x) and dried. The supports were removed from the column and treated with TFA/DCM/dimethyl sulfide (2 ml, 14:5:1). The high proportion of dimethyl sulfide was added as a carbonium ion scavenger. One concern was that the Tmob carbonium ion might alkylate susceptible residues (Tyr in this case) and cause impurities. In the presence of the dimethyl sulfide, absolutely no color was produced during cleavage which is indicative of the efficiency of this scavenging reagent.

After 2 hours, the suspensions were filtered through glass fiber and the filtrates blown to dryness under nitrogen. The residues were lyophilized from glacial acetic acid to give the peptides as white powders. HPLC's were run on Vydac 218 TP 54.6 5 micron C-18 reverse phase HPLC at 1.7 ml per minute, detection at 230 nm, buffer A is 0.05% TFA in water, buffer B is 0.05% TFA in acetonitrile, gradient runs at 5% B for 3 minutes, then changes linearly to 100% B over the next 20 minutes. Amino acid analyses (hydrolysis at 110° C. for 18 hours in 6M HCl plus 1% phenol) was determined on LKB Alpha Plus. The results are shown in Table 1.

TABLE 1

| Run | Support & Wt | | Method | Yield mg | Amino Acid Analysis | | | | | | |
|-----|--------------|---|--------|----------|------|------|------|------|------|------|------|
| | | | | | Val | Glx | Ala | Tyr | Ile | Asx | Gly |
| A | Porasil 150 mg | D367E | Asn/Gln PFP's* | 6.3 | 0.96 | 1.02 | 1.96 | 0.97 | 2.05 | 2.00 | 1.24 |
| B | Porasil 150 mg | D367E | Asn/Gln Tmob | 9.6 | 0.96 | 1.01 | 1.97 | 1.04 | 2.09 | 2.00 | 1.12 |
| C | MBHA 50 mg | D8021 | Asn/Gln PFP's* | 12.1 | 1.02 | 1.02 | 2.01 | 1.06 | 2.17 | 2.00 | 1.15 |
| D | MBHA 50 mg | D8021 | Asn/Gln Tmob | 17.8 | 0.93 | 0.96 | 1.97 | 1.06 | 2.19 | 2.00 | 1.15 |
| E | Pepsyn K D9007K | 100 mg | Asn/Gln PFP's* | 10.5 | 1.02 | 0.97 | 2.01 | 1.08 | 2.28 | 2.00 | 1.24 |
| F | Pepsyn K D9007K | 100 mg | Asn/Gln Tmob | 11.8 | 0.95 | 0.96 | 1.98 | 1.01 | 2.07 | 2.00 | 1.20 |

*Gln-PFP at 0.2 M not totally soluble in 0.3 M HOBt in DMF, supernatant used.

The amino acid analysis results show that the method performs outstanding well with all 3 supports. The conclusions are supported by the HPLCs which are shown as FIGS. 2A, 2B, 2C and 2D for Runs C, D, E and F, respectively. The product is present in Runs A and B but is obscured by several UV absorbing impurities. Apparently the presence of DMS in the TFA cleavage reagent causes some stripping of the hydromethylphenoxyacetic acid linker from the support. The results clearly and unambiguously show that Asn(Tmob) and Gln(Tmob) can be used in Fmoc mediated solid phase peptide synthesis. Direct DIPCDI mediated coupling can be used throughout the synthesis. All Fmoc derivatives are stable in solution.

Example 4

Figure 3:
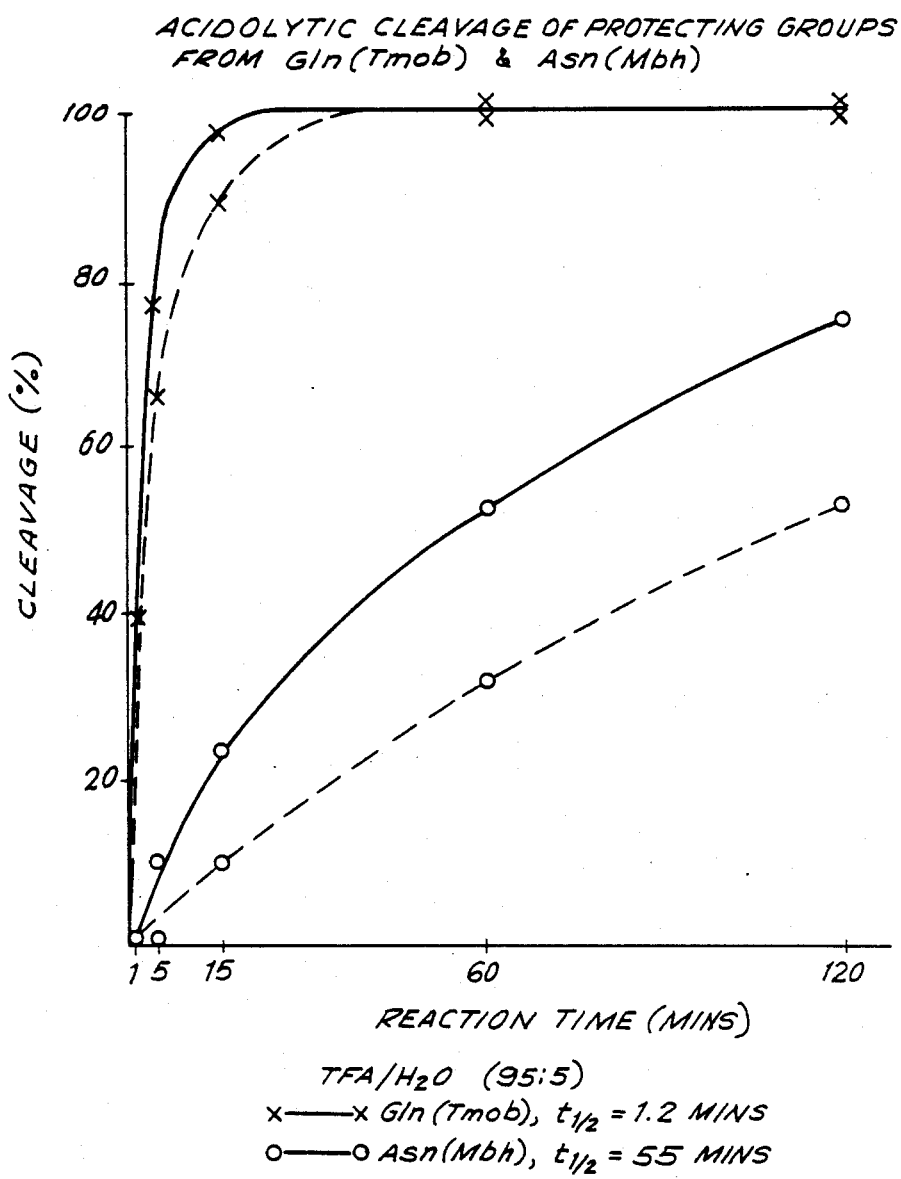
FIG. 3 is a graph showing the rate of acidolytic cleavage of protecting groups from Gln(Tmob) and Asn(Mbh)

Studies using TFA/H$_2$O (95:5) to cleave the Tmob protected acids from the support showed a half life of cleavage of Gln(Tmob) of ca. 1 min monitored by amino acid analysis and the bright orange color of the liberated trimethoxybenzylcarbonium ion. Use of TFA/dimethyl sulfide/dichloromethane (14:1:5) suppresses color formation and is deemed a more satisfactory reagent for use with peptides containing alkylatable side chains. A comparison was conducted of the relative rates of cleavage of Tmob and Mbh groups from the side chains of Asn and Gln using these two reagents. In the first two experiments, samples of an equal Molar mixture of Gln(Tmob) and Asn(Mbh) were treated with the reagents containing a known amount of valine as a standard. Twenty microliter aliquots were removed, added to cold water, snap frozen and lyophilized. Amounts of Asn and Gln liberated were determined by amino acid analysis. The results are depicted graphically in FIG. 3.

Example 5

In the second two experiments, samples of an equal Molar mixture of Asn(Tmob) and Gln(Mbh) were treated identically. Asn(Tmob) is cleaved 10 to 20 times more rapidly than Asn(Mbh) as depicted graphically in FIG. 4.

An exact comparison of the cleavage rates of Gln(Tmob) and Gln(Mbh) in Examples 4 and 5 is complicated by the presence of 17% free Gln in the commercial sample of Gln(Mbh) used as well as the possible presence of other impurities. Nevertheless, Gln(Tmob) is cleaved significantly more efficiently, i.e. between 50 and 100 times more rapidly than the Gln(Mbh) derivative.

These observations demonstrate the suitability and superiority of Tmob protection for Asn and Gln in solid phase peptide synthesis, specifically, Fmoc mediated SPPS. The slow cleavage of the corresponding Mbh derivatives makes these unattractable alternatives for routine application. A single method of coupling may now be used for every residue in the sequence and classes of difficult to synthesize peptides are eliminated. Routine use will result in a simplification in operating procedures coupled with a higher overall purity of product.

It will thus be seen that the objects set forth above, among those made apparent from the preceding description, are efficiently attained and, since certain changes may be made in carrying out the above method and in the composition set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients wherever the sense permits.

What is claimed is:

1. A trialkoxybenzyl protected amino acid for solid phase peptide synthesis having the formula:

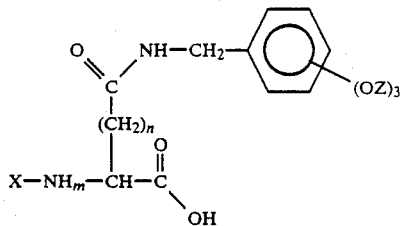

wherein n is 1 or 2; m is 0 or 1; Z is an alkyl group having from one to ten carbon atoms or combinations thereof; and wherein X is selected from the group consisting of α-fluorenylmethoxy-carbonyl (Fmoc), 2-(4-biphenyl)2-propyloxycarbonyl (Bpoc) and 2-phenyl-2-propyloxycarbonyl (Poc).

2. A trialkoxybenzyl protected amino acid of claim 1, wherein Z is a methyl group.

3. A trialkoxybenzyl protected amino acid of claim 2, wherein X is Fmoc.

4. A trialkoxybenzyl protected amino acid for solid phase peptide synthesis having the formula:

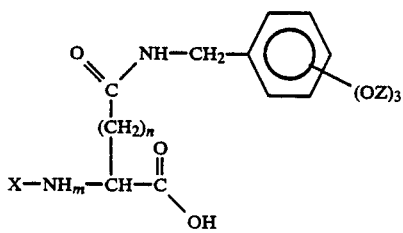

wherein Z is an alkyl group having from 1 to 10 carbon atoms or combinations thereof, n is 1 or 2, m is 0 or 1 and X is α-fluorenyl methyloxycarbonyl (Fmoc).

5. A trialkoxybenzyl protected amino acid of claim 4, wherein z is methyl.

6. A trialkoxybenzyl protected glutamine or asparagine having the formula:

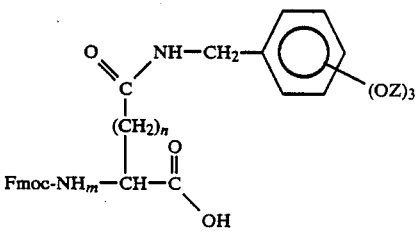

wherein n is 1 or 2, m is 1 and Z is a methyl group.

* * * * *